(12) United States Patent
Badju

(10) Patent No.: US 7,847,950 B2
(45) Date of Patent: Dec. 7, 2010

(54) METHOD AND A SYSTEM FOR GENERATING THREE- OR TWO-DIMENSIONAL IMAGES

(75) Inventor: Trajan Badju, Hisings Backa (SE)

(73) Assignee: Thorlabs Sweden AB, Gothenburg (SE)

( * ) Notice: Subject to any disclaimer, the term of this patent is extended or adjusted under 35 U.S.C. 154(b) by 550 days.

(21) Appl. No.: 11/576,843

(22) PCT Filed: Oct. 6, 2005

(86) PCT No.: PCT/SE2005/001478

§ 371 (c)(1),
(2), (4) Date: Jul. 30, 2007

(87) PCT Pub. No.: WO2006/038876

PCT Pub. Date: Apr. 13, 2006

(65) Prior Publication Data

US 2008/0195336 A1 Aug. 14, 2008

(30) Foreign Application Priority Data

Oct. 8, 2004 (SE) .................................. 0402435

(51) Int. Cl.
*G01B 9/02* (2006.01)
(52) U.S. Cl. ...................................... 356/479
(58) Field of Classification Search .................. 356/479, 356/497
See application file for complete search history.

(56) References Cited

U.S. PATENT DOCUMENTS

| | | | |
|---|---|---|---|
| 5,823,942 A | 10/1998 | Toida | |
| 5,956,355 A | 9/1999 | Swanson et al. | |
| 6,160,826 A | 12/2000 | Swanson et al. | |
| 6,501,551 B1 | 12/2002 | Tearney et al. | |
| 7,375,821 B2 * | 5/2008 | Han et al. | 356/497 |
| 2007/0076219 A1 * | 4/2007 | Toida | 356/511 |

FOREIGN PATENT DOCUMENTS

| | | |
|---|---|---|
| WO | 98/08048 A1 | 2/1998 |
| WO | 2005/031289 A1 | 4/2005 |

OTHER PUBLICATIONS

International Search Report, mailed Dec. 20, 2005, in connection with International Application No. PCT/SE2005/001478.

* cited by examiner

*Primary Examiner*—Tarifur Chowdhury
*Assistant Examiner*—Jonathon D Cook
(74) *Attorney, Agent, or Firm*—Graham Curtin, P.A.

(57) ABSTRACT

In a method and a system for generating images a laser being tuneable at a rapid frequency and a corresponding synchronized detector are provided. In a preferred embodiment the tuneable laser and the detector are synchronized in time so that the wavelength from the tuneable laser is known when the detector is given its detected signal value. In accordance with another preferred embodiment the tuneable laser is a monolithic laser, and in yet another preferred embodiment the laser and the detector are located on a common chip module. The system can be used to generate OCT images.

17 Claims, 3 Drawing Sheets

METHOD AND A SYSTEM FOR GENERATING THREE- OR TWO-DIMENSIONAL IMAGES

This application is a national-phase counterpart filed under 35 U.S.C. §371 of International Patent Application No. PCT/SE2005/001478 filed on Oct. 6, 2005. This application claims the benefit of the filing date of that application. This application also claims priority to Swedish Patent Application No. 0402435-2 filed on Oct. 8, 2004.

TECHNICAL FIELD

The present invention relates to a method and system for generating two- and three-dimensional images, and in particular to a system using Optical Coherence Tomography (OCT) technology.

BACKGROUND OF THE INVENTION

In many applications there is a need and desire to generate and display three-dimensional images. One area of particular interest is as an aiding tool in surgery and similar applications such as in-vivo diagnosis.

For many years the predominant tools for generating two- and three-dimensional images have been the microscope or/and an ultra-sound instrument. However, the drawback with a microscope is that tissue has to be brought to the microscope thereby making it impossible to perform in-vivo examination. For ultra-sound techniques the drawback is the coarse resolution.

Further, many diseases such as cancer in various forms are best examined at very high resolution. For many years a need existed to provide images with high resolution from within the body. This problem was partially solved by the development of Optical Coherence Tomography (OCT) technology.

U.S. Pat. Nos. 5,956,355 and 6,160,826 are examples of systems relying on OCT technology for generating images.

However, there are numerous problems and drawbacks with existing OCT based image-generating systems. In particular the existing systems are unable to generate fast and high accuracy two dimensional scans or three-dimensional images in real time. Thus, whereas it is entirely possible to overlay a number of two-dimensional (2-D) images and thereby form a three-dimensional (3-D) image, such an approach will not generate 3-D images in real time.

Real time 3-D images would be very useful and a powerful tool, for example for assisting in surgery. A number of other application areas exist, such as retina examinations, cancer diagnosis, diagnosis of industrial processes, etc.

Another problem encountered in prior systems is their relatively large size. For example, it is common for a system relying on opto-mechanical components to have a size of more than 10 dm$^3$.

SUMMARY

The object of the present invention is to overcome the problems as outlined above and to provide a method and a system, which enables generation of 3-D images in real time in an OCT-based, or similar interferometer-based image generation system.

It is a further object of the present invention to provide a scanning device, that scans the surface of the intended volume/body to be examined that is small and compact and which can even be entered into a human body.

These objects are obtained by a method and a system comprising a laser being tuneable at a rapid frequency and a fast broad band detector.

In a preferred embodiment the tuneable laser and the fast broad band detector are synchronized using a synchronizing controlling unit correlating the laser with the detector at each wavelength sample.

In accordance with another preferred embodiment the tuneable laser is a monolithic laser, and in yet another preferred embodiment the laser and the detector are located on a common chip module which also can include the synchronizing controlling unit.

BRIEF DESCRIPTION OF THE DRAWINGS

The present invention will now be described in more detail by way of non-limiting examples and with reference to the accompanying drawings, in which.

DESCRIPTION OF PREFERRED EMBODIMENTS

Figure 1:
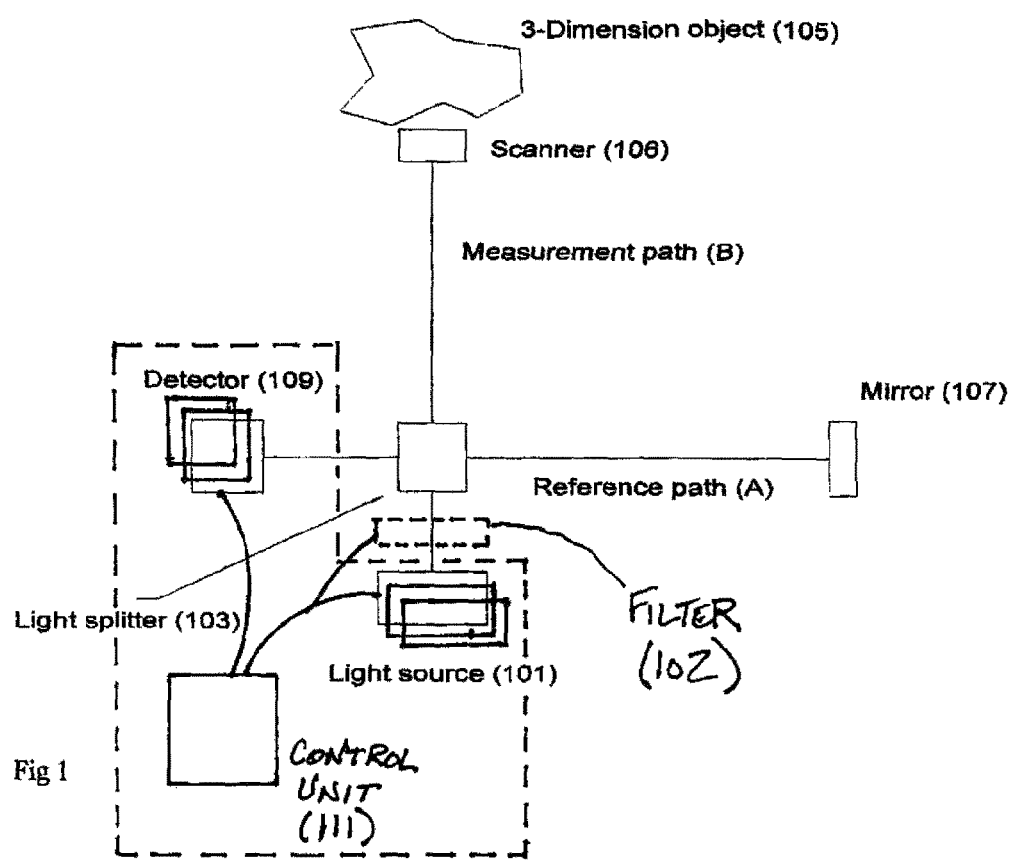
FIG. 1 is a general view of an exemplary 3-D image generation system.

In FIG. 1, a general view illustrating an exemplary set up of an image generation system in accordance with the present invention is depicted. The system comprises a light-emitting source 101. It is preferred to use a rapidly tuneable laser as the light-emitting source 101. In particular it is preferred to use a monolithic laser. An example of a suitable rapidly tuneable monolithic laser is the Syntune laser, S 1000.

The exemplary laser depicted in FIG. 1 is able to change wavelength at a high rate e.g. 20 kHz. Higher rates are possible to achieve if the application is such that a higher rate would be advantageous. Today rates in the MHz range are entirely possible. The tuneable light source can also be connected and synchronized with the tuneable filter 102 in order to reduce the optical noise, SSE (Stimulated Source Emission).

For example the laser 101 can be set to continuously generate light in for example the range 1250 nm to 1350 nm, a range suited for medical applications relating to skin tissues. Other wavelength ranges can be used depending on the application and the material to be investigated. Another suitable range is around 1550 nm The laser is set to sweep between these wavelengths at a rate that generates each wavelength in the range 1250 nm to 1350 nm two times per time period. The time period T being ½₀ Khz=0.05 ms.

Figure 3:
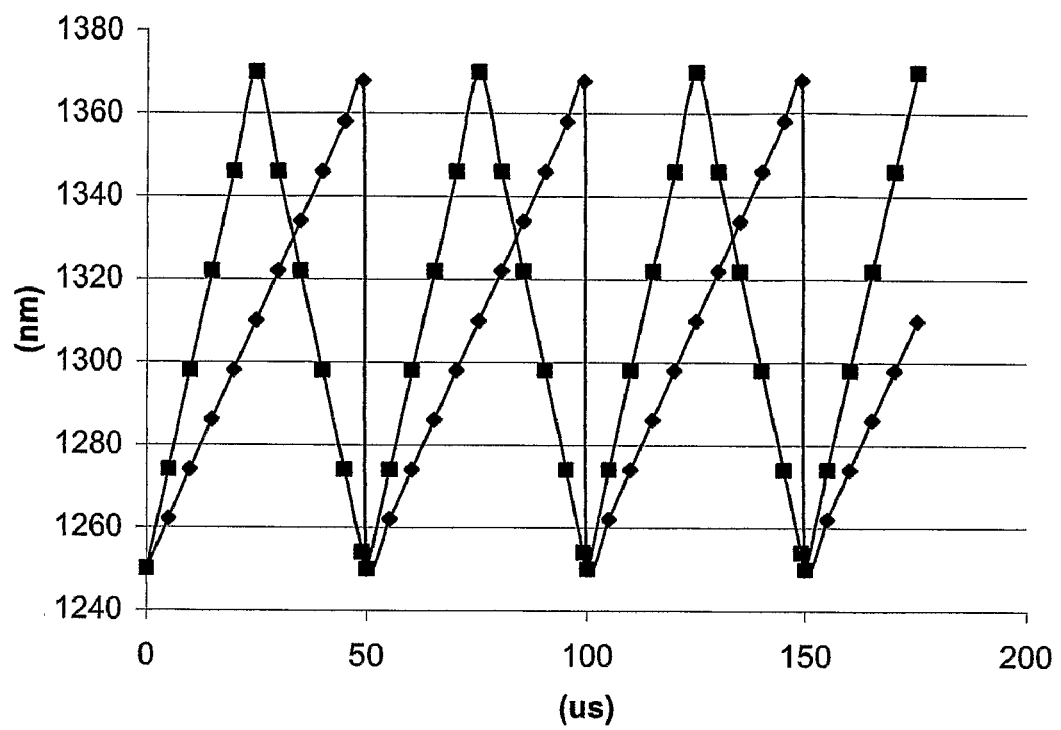
FIG. 3 illustrates different sweep patterns
Figure 4:
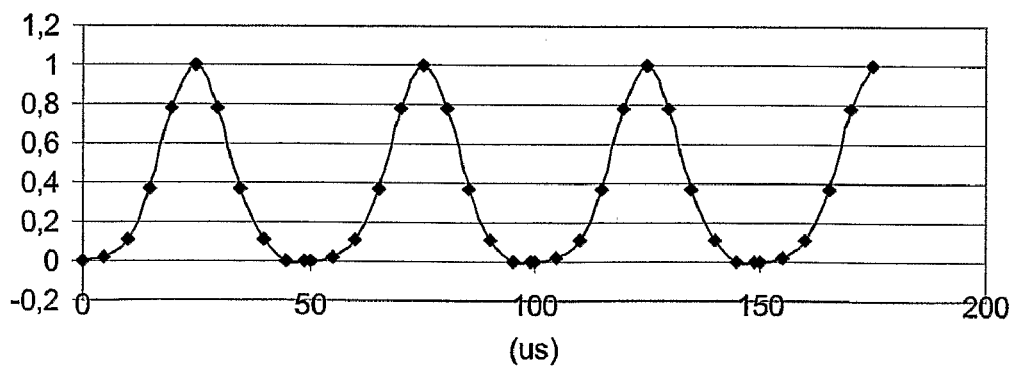
FIG. 4 illustrates a laser power that varies in accordance with a gaussian pattern.

The sweeps can be generated in any suitable fashion. Depending on the application a suitable sweep pattern is selected. This can be accomplished using an electronically controlled laser. In currently preferred embodiments the sweeps are generated either as repeated mono-directional sweeps starting at a first frequency, linearly sweeping to a second frequency and then restart at the first frequency or bi-directional starting at a first frequency linearly sweeping to a second frequency and the linerarly sweeping back to the first frequency and then restart, see FIG. 3. The power from the laser can be constant, be varied in accordance with a gaussian pattern, see FIG. 4 or any other suitable pattern.

The light emitted from the laser 101 is split into two separate paths, for example using a light splitter 103. The two paths exiting the light splitter 103 are led into separate light paths A and B, respectively. The paths A and B can be formed by optical fibres, waveguides, free space in air or gases and/or glass or a suitable combination thereof. The light directed through path A is used as reference as will be described below and the light directed through the path B is directed at an object 107 for which a 3-D image is to be generated of. At the end of the optical path B a Scanner 106 is located.

The object 107 is a three-dimensional object to be measured. Light reflected by the object is returned through the optical path B and directed to a detector 109. The detector can advantageously be the detector described in the co-pending Swedish patent application No. 0302577-2 entitled "Photodetector". In a similar manner light reflected by a mirror 105 at the end of the optical path A is also directed to the detector 109.

Finally, there is a control/data sampling unit 111 provided for synchronizing the laser 101 and the detector 109 and for collecting data for output as an image of the object 107.

Figure 2:
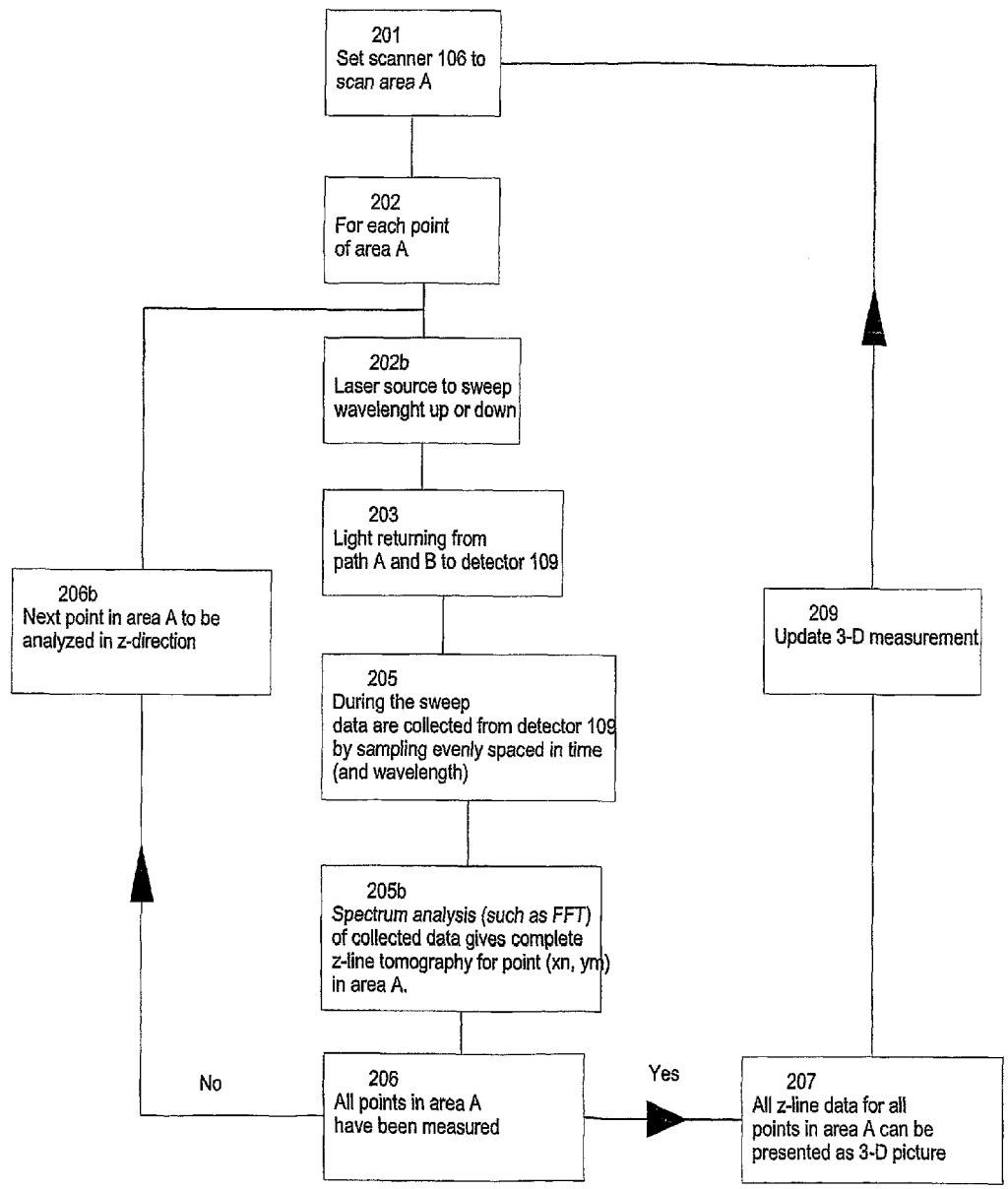
FIG. 2 is a flowchart illustrating different steps carried out in the system depicted in FIG. 1 when generating images.

In FIG. 2 a flow chart illustrating the different steps performed in the system depicted in FIG. 1 when generating a three-dimensional image is shown. In the example used it is assumed the an object to be measured over a volume $V(x,y,z)$ where x,y denotes the area seen by a two-dimensional scanner and z is the depth perpendicularly into that area. It is further assumed that the Volume V is measured using for example 500×500×500 pixels, the number of sample points is depending on the body to be examined and the wanted resolution.

First in a step 201 the scanner 106 is set to scan an area comprising e.g. 500×500 pixels. For each pixel the depth z of the object 107 is measured using a wavelength sweep of the laser 101, step.

Thus, during a time period T light reflected from the object 107 is returned to the detector 109. (Note that the laser 101 being a monolithic laser can be tuning up and down in wavelength at a constant speed $V=2*lambda_{band}/T$, but it can also be set to tune the wavelength in one direction, from short to long, and then start at the shortest wavelength again or vice versa.), step 202 b At the same time light reflected from the mirror 105 is also returned to the detector in a step 203. Data values are collected from the detector 109 at certain pre-determined times at which the current wavelength of the laser is known, step 205. For example, if as in this example 500 data values evenly distributed over z are to be collected, 500 data values have to be collected during one half of a time period T. In this example where the laser is set to sweep with a frequency of 20 kHz a new data sample needs to be collected each 50 ns.

Spectrum analysis, for example a FFT of the collected data then gives complete z-line tomography for each point x,y in the area A, step 205b and 206.

After one half of a time period T, 25 µs, the next pixel of the 2-dimensional scanner 106 can have its z-line measured. Thus in 500×500×25 µs=6.25 s. This time can easily be reduced by letting the laser sweep at a higher rate.

Finally in a step 207 the three-dimensional image of the object 107 is output. In a preferred embodiment the image is then continuously updated, step 209, thereby creating a 3-D video sequence of the object in real time.

When generating the 3-D image it is important that the detector and laser are synchronized so that the correct data value is collected at the correct time. It is preferred to use a monolithic laser as the laser 101 because it is then possible to obtain direct electronic control of the wavelength thereby making the synchronization between the laser and the detector easy and fast. Other types of lasers e.g. ECLs can be used but are currently less preferred because the wavelength then has to be defined indirectly. Also, as noted below a monolithic laser can be integrated on an integrated circuit thereby making the implementation very small indeed.

The generation of the samples in the z-direction relies on the following. If, at a particular wavelength generated by the laser one path (A, B) is not equal in length to the other the different received reflected light from the two sources of reflection, i.e. the object to be measured 107 and the mirror 105 will be out of phase when detected by the detector. Thus, the amplitude will vary at the detector will vary as a function of the difference in length of the two paths in a pattern typical to an interferometer.

Thus, the amplitude will vary as a sine function with a maximum when the paths have the exact same length and when the difference is equal to a multiple of the current wavelength emitted by the laser. Hence, the period for the varying amplitude in the combine optical signal returned from the mirror 105 and the object 107 will depend on the current wavelength emitted by the laser. It should be noted that the light returned from the two paths will at all time have the same wavelength. For this reason the signal generated by the detector will be a DC-signal when the light generated by the laser is constant in wavelength.

If, on the other hand the wavelength of the light emitted by the laser is varying in frequency so the emitted wavelength is a function of time $\lambda(t)=f(t)$ the following will occur.

If the paths are of equal length, there will be no difference in the phase of the two reflected light signals. Thus, the combined signal will be both a maxima and also be a DC-signal (as for the case described above with a fixed wavelength)

If there is a small difference in length between the paths, the light reflected from the different sources (object 107 and mirror 105) will arrive at the detector slightly out of phase thereby resulting in somewhat smaller amplitude, but also they will differ in wavelength due to the variation in emitted wavelength from the laser.

Since the emitted wavelength is constantly varying, i.e. the laser sweeps at a constant rate between two wavelengths, the light received at the detector from the longer of the two paths (if there is a difference) will at the time t1 vary as:

$$\lambda_{longpath}(t1)=\lambda(t_1-\Delta1/c)$$

As a result the signal detected by the detector 109 will have a frequency equal to the difference in frequency between the two signals received via path A and B, respectively. Assuming that the sampling frequency is higher than the shift in wavelength for the laser 101, the detector will detect this signal. That is a signal out of phase and having a frequency equal to the difference in frequency between the two signals. Provided that a constant sweep rate is used for the laser 101 and that the samples are sampled at constant time intervals, the phase difference will vary, but the difference in frequency between the two received signals will remain the same.

The resulting signal, sometimes termed the beat signal, detected at the detector 109 will hence be a sine signal sampled at a very high rate, varying with a frequency that depends on the difference in path length between the two paths A and B, the wavelength emitted by the laser 101 and the sweep frequency of the laser 101.

Further, assume that the object 107 is replaced by a number n of mirrors each reflecting the light back to the detector. The detector will then receive n+1 optical signals. The light received by the detector will then have different wavelengths, one wavelength corresponding to each mirror. For example if the object 107 is replaced by three mirrors there will be three reflected optical signals from those and one signal from the reference mirror associated with path A. The three reflected signals will result in three different beat frequencies (the beat frequency between the three from path b and the one from path a) for each sample. Using Fourier transformation of the sampled signal during one half time period T, it is then possible to obtain a position for all three mirrors. This is possible because there will be particular beat frequency component s corresponding to each mirror and its corresponding position as mentioned above. Moreover the amplitude for each frequency will correspond to the amount of light reflected by each mirror, the more light reflected by a particular mirror the higher the amplitude detected by the detector.

In case the mirrors are instead tissue, more dense tissue will reflect more light and hence create higher amplitude at the detector. Scanning over an area will provide a full 3D image of the volume under examine.

When using the system as described herein it is advantageous and preferred that the light emitting source can generate high frequency sweeps in a repeatable manner at a constant power or variable power as described above during the entire sweep. Further, the detector should preferably have good high bandwidth thereby be able to detect optical signals at a high rate (many samples per second) and also have a broad wavelength sensitivity that corresponds to the wavelength generated by the light emitting source. The system as described herein can generate output signals at a rate of MHz or more. It is also preferred to use a large range for the wavelength sweep since this will provide a better resolution in the z-direction (depth) because the greater the difference in frequency between different depths, the easier they will be to separate in the resulting spectrogram.

Also as noted above, in order to provide useful results it is preferred that the time sampling is made at constant intervals and that the laser used has a line width being smaller than the difference in light frequency between two time samples.

The size of the apparatus can be minimized to a size that makes it possible to be easily moved from one location to another and even be used outside in a harsh environment. The scanning device 106 can also be made small and compact by using a Micro-Electro-Optical-Mechanical-System (MOEMS) so it is possible to insert the scanning device into the human body or other bodies and devices that need to be examined from the inside.

Furthermore, the system as described herein can be implemented using two or more light sources, two or more detectors, and two and more optical filters. Each light source having its specific wavelength or wavelength range and each detector will only detect one wavelength or wavelength band by using the appropriate optical filter. In particular if three tuneable lasers and three detectors are employed colour images can be obtained. For example, each tuneable laser is set to its own wavelength band, and each detector signal is encoded as colour signal, like the Red, Green and Blue (RGB) encoded system for generating a true coloured 2-D or 3-D image.

Further using the approach with several lasers operating in different wavelength bands it is possible to apply one colour for cancer tissue one for fluids and yet another for fat tissue, etc. This because different tissue will reflect different wavelengths differently.

In yet another embodiment a multiple frequency system is provided by transmitting at least two different laser frequencies in a time division pulse train. So that a first frequency is transmitted during a first time interval and a second frequency during a second time interval, etc.

When detecting the response of laser pulses generated in this manner, each laser pulse is detected separately by a detector that is synchronized with the transmitted laser pulse train. In the alternative a multitude of detectors one for each frequency or a combination thereof can be used.

In the event synchronization of a detector is required, this can advantageously be provided by the control system.

Using the method and system as described herein will provide excellent three-dimensional images of a vide range of different objects including tissues of various kinds on and inside the human body as well as other living animals and plants. The system will be a great help in different diagnosis systems including skin cancer, heart, brain and lung conditions to name a few. Other possibilities to use the described system herein, both using 2-D and 3-D scans, are; process industry like plastic, glass, pulp, steel and other materials that need to be inspected for cracks, uniformities, and contamination.

The invention claimed is:

1. A system for generating images, comprising:
    a monolithic tunable light source;
    a first light path connected to the monolithic tunable light source, the first light path being associated with a mirror;
    a second light path connected to the monolithic tunable light source;
    a detector located to receive light from the first and second light paths;
    a controller configured to synchronize the monolithic tunable light source and the detector; and
    an output unit for generating a three-dimensional (3-D) or two-dimensional (2-D) image in response to signals received from the first and second light paths;
    wherein the monolithic tunable light source and the detector are integrated on a common chip module.

2. The system of claim 1, wherein the light source and detector are integrated on a common chip.

3. The system of claim 1, wherein the system is an optical coherence tomography (OCT) system.

4. The system of claim 3, further comprising a scanner device.

5. The system of claim 1, further comprising a control unit for controlling and synchronizing a wavelength of the light source and/or activating at least one of the light source and the detector.

6. The system of claim 1, further comprising a tunable optical filter.

7. The system of claim 6, further comprising a second light source, a second detector, and a second optical filter, wherein each of the light sources has a respective wavelength and each of the detectors use a respective optical filter to detect only one of the respective wavelengths.

8. The system of claim 7, wherein the light sources are configured to transmit pulse trains of different frequencies.

9. A system for generating a three-dimensional (3-D) image, comprising:
    a monolithic tunable light source;
    a first light path connected to the monolithic tunable light source, the first light path being associated with a mirror;
    a second light path connected to the monolithic tunable light source;
    a detector connected to the first and second light paths;
    a controller configured to synchronize the monolithic tunable light source and the detector; and
    an output unit for generating a 3-D image in response to a detected frequency and a frequency of the monolithic tunable light source;
    wherein the monolithic tunable light source and the detector are integrated on a common chip module.

10. The system of claim 9, wherein the light source is a monolithic laser.

11. The system of claim 9, wherein the light source and detector are integrated on a common chip.

12. The system of claim 9, further comprising a scanner device.

13. The system of claim 9, further comprising a control unit for controlling and synchronizing a wavelength of the light source and/or activating at least one of the light source and the detector.

14. The system of claim 9, further comprising a tunable optical filter.

15. The system of claim 14, further comprising at least one additional light source, at least one additional detector, and at least one additional optical filter, wherein each light source has a respective wavelength and each detector uses a respective optical filter to detect only one of the respective wavelengths.

16. The system of claim 15, comprising three light sources and three detectors, wherein each light source is a tunable laser set to a respective wavelength band, and each detector generates a signal encoded as a color signal.

17. The system of claim 15, wherein the light sources are configured to transmit pulse trains of different frequencies.

* * * * *